United States Patent [19]

Waller et al.

[11] Patent Number: 4,806,575

[45] Date of Patent: * Feb. 21, 1989

[54] PREVENTION OF OUTGASSING IN POLYVINYLSILOXANE ELASTOMERS BY THE USE OF FINELY DIVIDED PLATINUM BLACK

[75] Inventors: Duncan E. Waller, Ypsilanti; Laurie D. Lovshe, Plymouth, both of Mich.

[73] Assignee: Kerr Manufacturing Company, Romulus, Mich.

[*] Notice: The portion of the term of this patent subsequent to Nov. 1, 2005 has been disclaimed.

[21] Appl. No.: 932,246

[22] Filed: Nov. 19, 1986

[51] Int. Cl.$^4$ .................................................. A61K 6/00
[52] U.S. Cl. ...................................... 523/120; 526/279; 526/266; 526/108; 526/241; 526/112

[58] Field of Search ................. 523/120; 526/279, 266, 526/108, 241, 112

[56] References Cited

U.S. PATENT DOCUMENTS 4,273,902  6/1981  Tomioka et al. .................... 525/478
4,600,751  7/1986  Lee ...................................... 526/279

Primary Examiner—Joseph L. Schofer
Assistant Examiner—Peter D. Mulcahy
Attorney, Agent, or Firm—Marjama & Pincelli

[57] ABSTRACT

A polyvinylsiloxane catalyst paste which comprises up to 20,000 ppm of finely divided platinum black which functions to adsorb hydrogen gas generated in the reaction of said catalyst paste with a hydrofunctional polydimethylsiloxane.

4 Claims, No Drawings

PREVENTION OF OUTGASSING IN POLYVINYLSILOXANE ELASTOMERS BY THE USE OF FINELY DIVIDED PLATINUM BLACK

BACKGROUND OF THE INVENTION

The liberation of small quantities of hydrogen gas from RTV addition cured polyvinylsiloxane elastomers, due to the reaction between the platinum catalyst and hydrofunctional polydimethylsiloxane, is a recognized problem. The evolution of the hydrogen gas results in the formation of pores in the model formed from the impression, producing an undesirable pitted surface.

In the U.S. Pat. No. 4,273,902, issued June 16, 1981, and assigned to G-C Dental Industrial Corp., of Tokyo, this problem is well described and a solution is claimed using 0.5 ppm or more finely divided palladium and/or a finely divided palladium alloy containing 10% by weight or more of palladium, without inhibiting the addition reaction. In Column 3, line 33 et seq., various other elemental metals are cited, including platinum, but are stated to be inferior to palladium and fail to eliminate the undesirable pores in the surface of the resulting model.

The adsorption of hydrogen by palladium is variously quoted as 502, 935 and even 2952 times its own volume, J. M. Mellor, Inorganic Chemistry Vol XVII 1947, page 616 et seq., while the adsorption of hydrogen by platinum black is quoted as 310 volumes in Vol. XVI. It therefore becomes apparent that these adsorption variabilities arise from differences in the available surface areas of the finely divided metals, but are not significant in the case of the polyvinylsiloxane elastomer application, since if sufficiently finely divided and present in adequate concentration, the adsorption saturation level will never be reached.

SUMMARY OF THE INVENTION

Accordingly, it has been discovered that when samples of extremely finely divided platinum black were obtained with the highest possible surface area, specifically $24M^2/gram$, and were compared with equal weight percent concentrations of palladium black, by incorporation in identical polyvinylsiloxane elastomer pastes they were found to be equally and completely effective, down to a concentration level of about 0.2 ppm by weight. An effective concentration range for the platinum black is about 0.2 to 20,000 ppm by weight. The size range for the platinum black should be as small as possible. A preferred size range for the platinum black is from about 18 to 28 Angstrom Units.

The use of platinum black in conjunction with the present invention is in controlling or preventing outgassing in all addition cured polyvinylsiloxane elastomers which are primarily used in making dental impressions.

The platinum black is used to adsorb gaseous hydrogen generated during the curing reaction, and generally at a concentration level of about 0.2 to 20,000 ppm. A preferred concentration range is from about 0.001 to 0.01 weight percent (i.e., 1,000 to 10,000 ppm). The platinum black is added or blended with the catalyst paste in any convenient manner such as illustrated in U.S. Pat. No. 4,273,902 which is incorporated herein by reference.

DETAILED DESCRIPTION OF THE INVENTION

The following example illustrates one embodiment of the present invention:

| BASE PASTE | | CATALYST PASTE | |
|---|---|---|---|
| Vinyl Polydimethyl-siloxane | 20% | Vinyl Polydimethyl-siloxane | 20% |
| Hydropolydimethyl Siloxane | 3% | Cyclic Vinyl Siloxane | 0.4% |
| Silica Filler | 70% | Chloroplatinic Acid Complex | 1.0% |
| Liquid Petroleum or other inert plasticizer | 7% | Platinum Black | 0.005% |
| | | Liquid Petroleum or other inert plasticizer | 7% |
| | | Silica or other inert filler | 71.6% |

The following illustrates suitable compositional ranges for the components of the base and catalyst paste.

| BASE PASTE | WT % | CATALYST PASTE | WT % |
|---|---|---|---|
| Vinyl Polydimethylsiloxane | 10–60 | Vinyl Polydimethylsiloxane | 10–60 |
| Hydropolydimethyl Siloxane | 1–10 | Cyclic Vinyl Siloxane | 0–2 |
| Silica Filler | 20–80 | Chloroplatinic Acid Complex | 0.1–5.0 |
| Liquid Petroleum | 0–15 | Platinum Black | 0.2–20,000 ppm |
| | | Plasticizer | 0–15 |
| | | Filler | 20–80 |

The following illustrates suitable compositional ranges for a cured dental impression material of the present invention.

| | WT % |
|---|---|
| Vinyl Polydimethylsiloxane | 10–60 |
| Cyclic Vinyl Siloxane | 0–1 |
| Hydropolydimethyl Siloxane | 0.5–5.0 |
| Filler | 20–80 |
| Chloroplatinic Acid Complex | 0.05–2.5 |
| Platinum Black | 0.1–10,000 ppm |
| Plasticizer | 0–15 |

Both base and catalyst pastes contain vinyl polydimethyl siloxane and silica or other similar inert filler(s) and the base paste contains a moiety of hydrofunctional polydimethylsiloxane whereas the catalyst contains both a chloroplatinic acid catalyst complex and platinum black, to adsorb any gaseous hydrogen formed during mixing of the pastes and curing of the impression.

A cured impression is produced by mixing the base paste and catalyst such as that illustrated by the Example, in a 1:1 or other suitable ratio to form a homogeneous plastic mass which is applied over the dentition and adjacent gingival tissue and allowed to cure during a time frame of several minutes prior to mouth removal. Models were made from impressions taken with the platinum black containing impression materials immediately after mouth removal and found to be free of pores in all cases at or above the 0.005 weight percent platinum level.

Impressions and resulting molds or models formed using the concept of the present invention result in a surface smoothness which is significantly better than those formed without the use of platinum black.

While the invention has been described in detail with respect to specific embodiments thereof, it will be understood by those skilled in the art that variations and modifications may be made without departing from the essential features thereof.

What is claimed is:

1. A vinyl polydimethylsiloxane catalyst paste which consists of about 0.2 to 20,000 ppm of finely divided platinum black having a surface area of about 24M$^2$/gram and a size range of about 18 to 24 Angstrom Units, which functions to adsorb hydrogen gas generated in the reaction of said catalyst paste with a hydrofunctional polydimethylsiloxane containing base paste.

2. A polyvinylsiloxane catalyst paste which consists of about 0.2 to 20,000 ppm of finely divided platinum black having a surface area of about 24M$^2$/gram and a size range of about 18 to 24 Angstrom Units which functions to adsorb hydrogen gas generated in the reaction of said catalyst paste with a hydrofunctional polydimethylsiloxane containing base paste, this catalyst paste having the following composition:

Vinyl Polydimethylsiloxane
Cyclic Vinyl Siloxane
Chloroplatinic Acid Complex
Platinum Black
Plasticizer
Filler.

3. A two component dental impression material which comprises the following:

|  | WT % |
|---|---|
| BASE PASTE |  |
| Vinyl Polydimethylsiloxane | 10–60 |
| Hydropolydimethyl Siloxane | 1–10 |
| Silica Filler | 20–80 |
| Liquid Petroleum | 0–15 |
| CATALYST PASTE |  |
| Vinyl Polydimethylsiloxane | 10–60 |
| Cyclic Vinyl Siloxane | 0–2 |
| Chloroplatinic Acid Complex | 0.1–5.0 |
| Platinum Black | 0.2–20,000 ppm |
| Plasticizer | 0–15 |
| Filler | 20–80 | and wherein said platinum black has a surface area of about 24M$^2$/gram and a size range of about 18 to 28 Angstrom Units.

4. A cured dental impression which comprises the following composition:

|  | WT % |
|---|---|
| Vinyl Polydimethylsiloxane | 10–60 |
| Cyclic Vinyl Siloxane | 0–1 |
| Hydropolydimethyl Siloxane | 0.5–5.0 |
| Filler | 20–80 |
| Chloroplatinic Acid Complex | 0.05–2.5 |
| Platinum Black | 0.1–10,000 ppm |
| Plasticizer | 0–15 | and wherein said platinum black has a surface area of about 24M$^2$/gram and a size range of about 18 to 28 Angstrom Units.

* * * * *